United States Patent [19]

Przybylowicz et al.

[11] Patent Number: 5,067,093
[45] Date of Patent: Nov. 19, 1991

[54] REFERENCE READING IN AN ANALYZER

[75] Inventors: Catherine S. Przybylowicz, Rochester; Edwin W. Brill, Jr., Pittsford; Luigi A. Carrozziere, Rochester, all of N.Y.

[73] Assignee: Eastman Kodak Company, Rochester, N.Y.

[21] Appl. No.: 469,887

[22] Filed: Jan. 24, 1990

[51] Int. Cl.⁵ .................... G01N 21/55; G06F 15/20
[52] U.S. Cl. .................... 364/498; 364/496; 364/571.04
[58] Field of Search .......... 364/498, 571.01, 571.04, 364/571.08, 579, 496, 497; 356/243, 448; 422/64

[56] References Cited

U.S. PATENT DOCUMENTS

| | | | |
|---|---|---|---|
| 3,902,052 | 8/1985 | Amar et al. | 235/151 |
| 3,960,497 | 6/1976 | Acord | 364/579 |
| 4,039,933 | 2/1977 | Moran | 324/29 |
| 4,043,756 | 8/1977 | Sommervold | 23/230 |
| 4,566,798 | 1/1986 | Haas | 356/243 |
| 4,627,014 | 12/1986 | Lo et al. | 364/571.01 |
| 4,678,755 | 7/1987 | Shinohara et al. | 436/43 |
| 4,916,645 | 4/1990 | Wuest et al. | 364/571.01 |

Primary Examiner—Parshotam S. Lall
Assistant Examiner—Ellis B. Ramirez
Attorney, Agent, or Firm—Dana M. Schmidt

[57] ABSTRACT

A method and apparatus are disclosed for reading a test element and a reference element in an incubator to insure that a) they are both read at the same wavelength and b) the reading at this wavelength of the reference element used to compare the test element reading, is the closest in point of time to the reading taken of the test element. In some cases, this requires the comparison with a reference element that is read after the reading of the test element.

8 Claims, 2 Drawing Sheets

REFERENCE READING IN AN ANALYZER

FIELD OF THE INVENTION

This invention relates to a method of machine-calibrating an analyzer against reference elements positioned in an incubator along with test elements, specifically to correct for drift in the light source.

BACKGROUND OF THE INVENTION

Analyzers detecting the amounts of analytes in certain body fluids use a light source to illuminate test samples, which sources can vary (drift) in intensity over time. Usually conventional solutions require a machine reference determination, or alternatively, simultaneous readings of the light source used to illuminate the test samples, herein identified as "dual channel". In many applications, the dual channel approach is not preferred, because of cost. Hence, a machine reference reading is usually used.

In making these machine reference readings, a conventional procedure has been to read the reference value, store it, thereafter read the test sample, and compare the two. The "comparison" conventionally involves, for example, the use of the formula (sample—reference$_{black}$)/ (reference$_{white}$—reference$_{black}$) as is listed in U.S. Pat. No. 4,566,798, column 1, line 40, where both a black and a white reference are used. Occasionally the reference element is read again to update that value, but the updated reading is only used for subsequent sample readings, and not previous sample readings. The problem is that the longer in time the reference reading is from the sample reading, the greater likelihood there is of drift in the light source.

We have discovered that this reference read procedure is not adequate. More specifically, the reference value tends to drift, and the drift is such that merely occasionally updating it does not adequately correct sample readings taken just prior to the update. Of course, a reference element could be positioned to be read every time and just prior to when a sample is to be read, but this is unsatisfactory as the number of reference readings would become too numerous. The end result would be increased cost for these reference elements and lack of through-put.

Yet another problem with many conventional analyzers is that, to make a reading of a sample at a new wavelength, say of 460 nm, it first needs to make a new reference element reading at that wavelength. Thus, every time a new wavelength is required for a new chemistry, a new reference element could be required for that new wavelength. Since only one wavelength can be used for a single scan of a reference element, if a new assay is added to an incubator with a single reference element, only previous or subsequent pass-throughs could generate a reading at the desired wavelength. As a result, there could be as many as 8 reference elements in an analyzer, for 8 different wavelengths used in the analysis. Such a multitude of wavelengths is not only expensive but occupies space that could otherwise be used for other purposes.

SUMMARY OF THE INVENTION

We have constructed an analyzer and a method for assaying analytes which overcome this reference drift problem, without requiring the reference to be read every time a sample is to be read.

More specifically, in accord with one aspect of the invention there is provided a method for quantitatively assaying for an analyte in a biological liquid, comprising the steps of
  a) scanning with a light beam a test element bearing a sample of liquid;
  b) scanning a reference element with the light beam;
  c) detecting the amount of light diffusely reflected from the test element and the reference element;
  d) filtering the light beam before or after reflection from the elements and before detection, at a preselected wavelength that is the same for both the test element and the reference element;
  e) storing the detected amounts of diffuse reflection for each scanning of the reference element and test element; and
  f) comparing the detected reflectance of the test element with the stored reference detected reflectance to determine how much analyte is present, the reference element being scanned repeatedly, each time for a predetermined multiple of test elements scanned.

This method is improved in that step e) comprises the steps of selecting from the stored reference reflectance detections at the wavelength that which is either detected by step c) at a point of time closest to the time at which the test element is scanned at the wavelength in step a), or that which is computed to be the equivalent reference reflectance at the actual time the test element reflectance was read, and comparing said selected reference reflectance detection in step f) with the detected test element reflectance, whereby the effect of drift in the reading of the reference element is minimized.

In accord with another aspect of the invention there is provided an analyzer for quantitatively assaying for an analyte of a biological liquid, the analyzer including
  a) means for scanning with a light beam a test element bearing a sample of liquid;
  b) means for scanning a reference element with the light beam;
  c) means for detecting the amount of light diffusely reflected from the test element and the reference element;
  d) means for filtering the light beam so that the light reflected from the elements is at a preselected wavelength that is the same for the test element and the reference element;
  e) means for storing the detected amounts of diffuse reflection for each scanning of the reference element and of the test element; and
  f) means for comparing the detected reflectance of the test element with the stored reference detected reflectance at the selected wavelength to determine how much analyte is present, the reference element being scanned repeatedly, each time for a predetermined multiple of test elements scanned.

This analyzer is improved in that the analyzer further includes means for selecting from the stored reference reflective detections, either the value detected at the point of time that is closest to the time at which the test element is scanned by the scanning means a), or that which is computed to be the equivalent reference reflectance at the actual time the test element reflectance was read, and for supplying this value to the comparing means f), whereby the effect of drift in the reading of the reference element is minimized.

Therefore, it is an advantageous feature of this invention that an analyzer and analytical method are provided which compensate for drifts occurring in the reference reading, without necessitating undue repetitions of reads of the reference element.

It is a further advantageous feature of this invention that such a method and analyzer minimizes the number of reference elements that are needed.

Other advantageous features will become apparent from the following description of the preferred embodiments, when read in light of the attached drawing.

DESCRIPTION OF THE PREFERRED EMBODIMENTS

Figure 1:
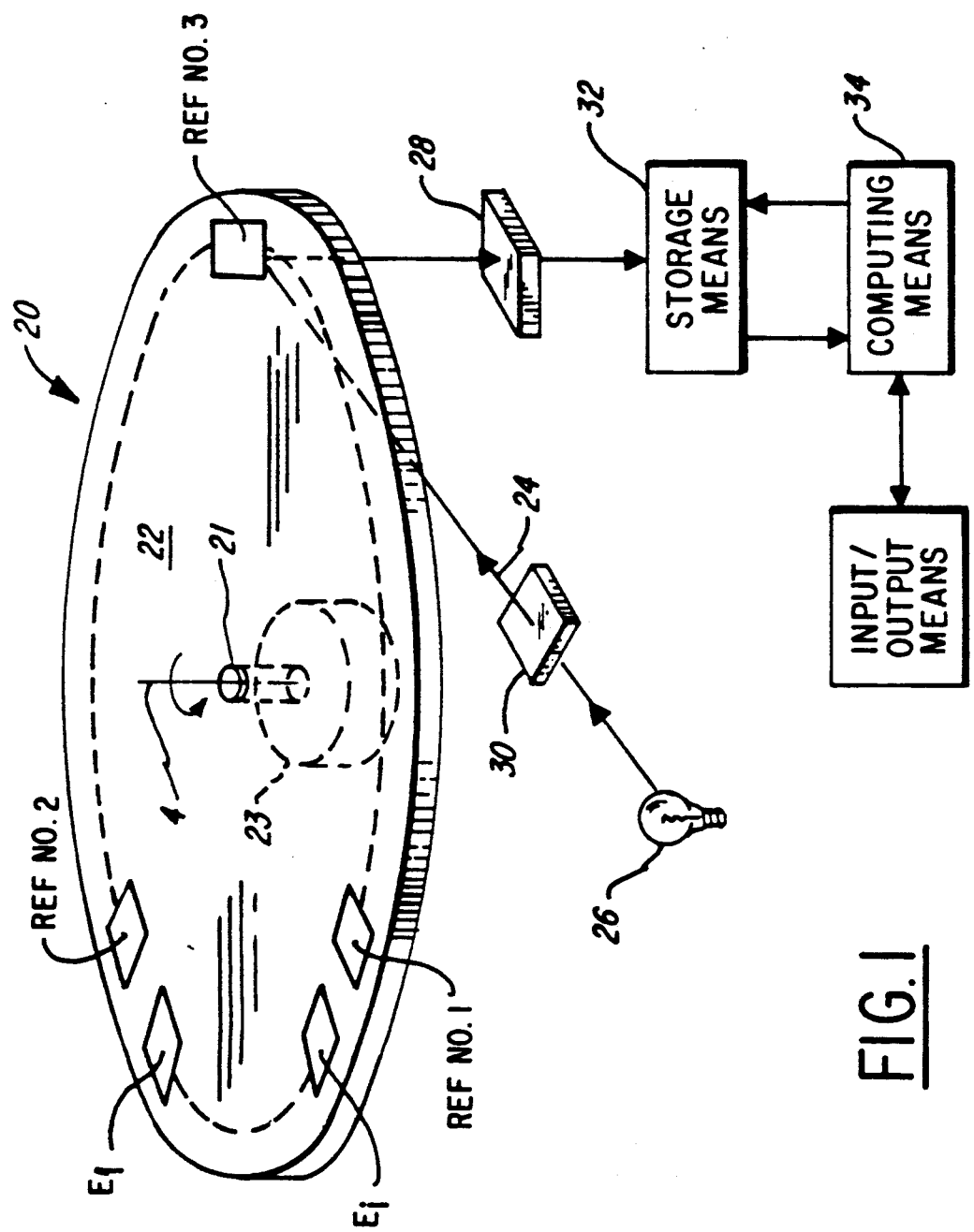
FIG. 1 is a schematic representation of an analyzer constructed in accord with the invention.

For purposes of discussion, analyzer 20, FIG. 1, is shown as having three reference elements and "i" test elements, positioned on a rotating support 22 mounted on shaft 21 driven by motor 23. A light beam 24 is generated by light source 26 off the plane of support 22, and a suitable detector 28 is also so positioned to detect only diffuse reflectance from each of the elements Ref. 1, Ref. 2, Ref. 3, and $E_1$, up to $E_i$ on support 22. Such an arrangement is conventional. Preferably, $E_1$ and up to $E_i$ can be either a colorimetric element or a rate element, and a mixture of both is usually present. Conventional means, not shown, are used to hold all the elements on support 22.

For purposes of discussion, the invention describes the use and comparison of reflectance R values. Alternatively, optical densities $D_R$ can also be used by the conventional conversion of $D_R = \log(1/R)$.

For simplicity, it is first assumed that only $E_1$ is present, that is "i" of $E_i$ is 1. Because the chemistry of $E_1$ can be greatly varied, as in the case of colorimetric assays or rate assays, and thus require scanning at any one of 8 predetermined wavelengths, the references are read at these 8 wavelengths to determine a reference reflectance detection against which the reading of $E_1$ is to be compared. A filter wheel of conventional structure is used to alternate between these desired wavelengths, providing an appropriate different filter 30 for each wavelength. Ideally, eight references could be provided, each optimized for reading at a preselected wavelength. Practically, however, only three reference coatings or elements are needed. Two are preferably identical (Ref. 2 and Ref. 3), and are preferably opal glass. The third, (Ref. 1), is opal glass coated with Inconel. In accord with one aspect of the invention each reference is read at more than one wavelength.

The readings proceed as follows, as support 22 is rotated about axis 4:

Assuming the first "read" occurs when "Ref. 1" moves into position under beam 24, it is read at 340 nm (using an appropriate filter 30). The value detected at detector 28 is stored in storage means 32 (and this occurs each time a scanning takes place). Next, element $E_1$ is read at whatever wavelength of the 8 herein discussed is appropriate to its chemistry. As support 22 continues to turn, Ref. 2 is read, at 400 nm. Then Ref. 3 is read at 600 nm. The second revolution of support 22 is then commenced, and Ref. 1 is read at 680 nm. $E_1$ is then read again at its wavelength (whatever it is), and so on through the values of Table 1. It is assumed that the elapsed time between each reading is the same, for example, about 6 sec.

TABLE I

| READ # | ELEMENT | NO. OF REVOLUTION | WAVELENGTH (nm) |
|---|---|---|---|
| 1 | Ref. 1 | 1st | 340 |
| 2 | $E_1$ | 1st | (predetermined for a particular assay) |
| 3 | Ref. 2 | 1st | 400 |
| 4 | Ref. 3 | 1st | 600 |
| 5 | Ref. 1 | 2nd | 680 |
| 6 | $E_1$ | 2nd | (same as read #2) |
| 7 | Ref. 2 | 2nd | 460 |
| 8 | Ref. 3 | 2nd | 630 |
| 9 | Ref. 1 | 3rd | 340 |
| 10 | $E_1$ | 3rd | (same as read #2) |
| 11 | Ref. 2 | 3rd | 540 |
| 12 | Ref. 3 | 3rd | 670 |
| 13 | Ref. 1 | 4th | 680 |
| 14 | $E_1$ | 4th etc. | (same as read #2) |

The fourth and subsequent revolutions simply repeat the sequences started at the first revolution.

The number of times $E_1$ has to be read will depend on the type of sample chemistry involved, and other factors. If it is an end-point element, theoretically it needs to be read only once - that is, when the color density is complete and no longer continues to increase. In such a case, read #2 above is taken after end-point is reached. If it is a rate chemistry, at least two readings are needed, to determine the rate of change. However, even the end-point test samples can benefit from reading more than once (after end-point), since then they can be compared internally for "outlier" readings, that is, to see if any of the multiple readings is so different as to be in error and discarded. An average can then be made of the remaining. Alternatively, and preferably, a line is regressed through those remaining and a value picked off this line at a selected time. Five readings is particularly useful. In fact, five readings of all $E_i$ for $i = 1$ to n is useful for all colorimetric elements. For each of the rate chemistries, 54 readings are taken.

Assuming however that $E_1$ from the preceding table is an end-point chemistry, is to be read at 540 nm, and needs only one such reading instead of an average, a choice has to be made from the multiple readings of the reference at 540. For purposes of the analysis, it is assumed that the time of reading No. 10, Table I, is the optimum time for reading $E_1$. With this, a choice has to be made which $E_1$ reference reading, at 540 nm, is to be saved and compared against, for example, the No. 10 reading of $E_1$. The answer is, the one closest in time, which for Table I is read No. 11. As is not unusual in this invention, the reading of the test sample that is recorded, saved and compared with the reading of the appropriate reference element, occurs before the reading of the reference element. This however is only because that reading of the test element is closest in time to the reading of the reference element, and thus most likely to be based on the same amount of light emitted from the reflectometer light source 26.

The problem is even more complicated for a large number of "i" in $E_i$, say $i = 24$, for the 3 references being read. Again, the choice to be made is, which reading of Ref. 1, Ref. 2 or Ref. 3 at wavelength X, is to be used. In accordance with this invention, the answer is, the one that exists closest in time to the time of reading ($E_i$)

i=n at wavelength X. As noted, this reading of the reference may well be one that occurs after the reading of the element at wavelength X. The microprocessor, or other computing means 34, FIG. 1, used to operate the analyzer, is programmed to recognize in advance when future reference readings will be made at the selected wavelength, and calculates whether the future reference read will be closer in time than one already made. If so, only the future reading of the reference need be stored and used to compare with the test element reading to convert the latter to a concentration.

Figure 2:
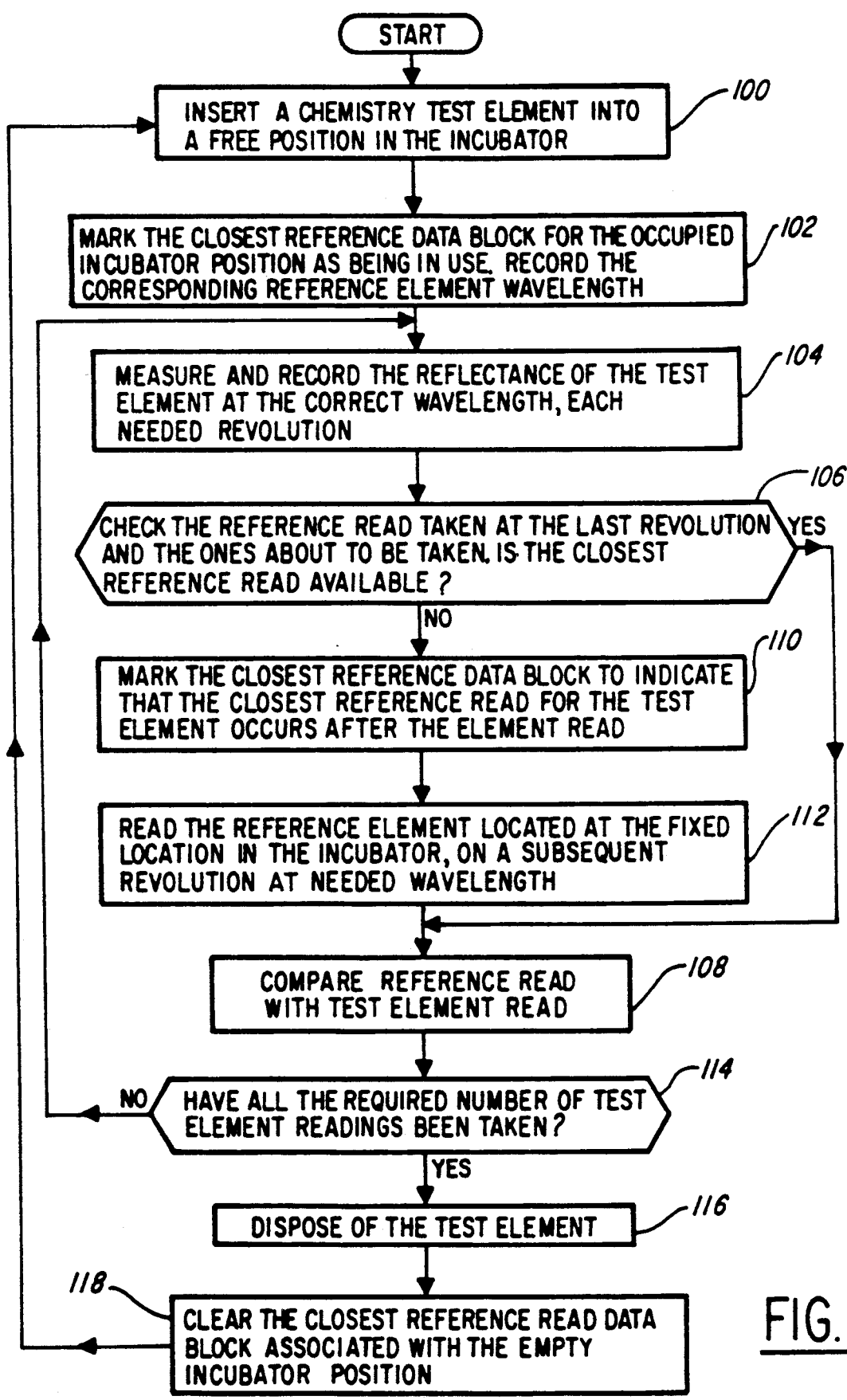
FIG. 2 is a flow chart depicting a preferred organization of the software useful in practicing the invention.

Any conventional method can be used to program computing means 34 to carry out the method of the invention. The logic flow chart of FIG. 2 is useful in setting up such a program. The first step 100, is to insert a test element into one of the positions $E_i$ on incubator 22, for example, position $E_g$. Step 102 requires the computer to store ("mark") the location of the reference data block. If the position $E_x$ in step 100 is $E_1$, then this is Ref. #2. Next, step 104, the reflectance of the test element in question is read during the "needed" revolutions at the correct wavelength by detector 28 and stored in storage means 32. (This is done five times centered at the optimum time, when that element position comes around again at that filtered wavelength. The readings are then stored. The analyzer is preprogrammed to know which revolutions are required for reading a given test element to obtain the five readings (if colorimetric) that will give the optimum read time).

At this point, an "if/then/else" query is used, step 106. Of the reference reflectance reading already taken during the last revolution of incubator 22 past beam 24, and of the reflectance reading about to be taken at this wavelength during this or the next revolution, is the one already taken, the one that is closest in point of time to the reading taken of the test element at this wavelength? If "yes", that reference reading as stored in means 32 is then compared in means 34 with the reading for the test element, step 108, and step 110 is skipped. Otherwise (or if "no"), steps 110 and 112 are followed, namely, computing means 34 notes that the closest reference reading is yet to be taken for that test element at position $E_g$.

In step 112, the reference elements that follow for this and following revolutions are then read at the wavelengths they are programmed for reading, until one of the reference elements is read at the needed wavelength. By definition (in step 106), this reading is closest in time to the reading of test element $E_x$. Thus, the next step is the comparing step 108, which has not yet been taken when the inquiry at 106 produces a "no" or an "else" response.

Following this, an "if/then/else" inquiry is taken at step 114, to determine if more readings of this test element at position $E_g$ are needed, or more accurately, if all needed reads have been taken. If "no", the process is iterative, except that in practice, step 104 may have already occurred during one of the subsequent revolutions taken during step 112 (assuming the answer to the inquiry at step 106 is "no"). Thus, in practice the reiteration of step 104 for the second and subsequent reflectance values of the test element at $E_g$ may simply be a look-up of such values as are already stored at means 32 and of their read times, so that step 106 can then be taken as to this subsequent iteration for the element at position $E_g$.

If the inquiry at step 114 is answered "yes", step 116 is followed to dispose of the test element, and then step 118 to "clear" the closest reference read associated with that empty position in the incubator. At this point, step 100 is repeated for a new test.

By the above procedure, all of the data points of the reads of the colorimetric test element $E_x$ have been taken, along with the reference element closest in time and at the same wavelength. At this point, computing means 34 is preferably used to do a detection of outliers and a line regression to achieve the optimum colorimetric value for $E_x$ at the optimum time.

With such data, the final comparison step of the reflectance value of the element $E_x$ and of the reflectance value of the reference can be made by means 34. This comparison of the reflectances produces a value of patient sample reflectance that is then correlated by conventional practices to produce an analyte concentration "reading" by any one of a variety of calibrations. That is, field calibrations may be used to check a "patient sample reflectance" so obtained using one or more liquids having known concentrations that are deposited on a test element similar to that used at $E_g$, or alternatively this may have been preset at the factory.

An equivalent method of obtaining the "closest-in-time" reference element reflection is as follows: the procedure is exactly the same, but the comparison of the actual test element $E_x$ reflectance is not made with an actually read reference reflectance. Instead, a reference reflectance $R_x$ computed to be closest-in-time to time $T_x$ (of the reading of element $E_x$) is used. This approach is a particularly useful alternative if lamp 26 is an incandescent lamp, such as a tungsten/halogen lamp. That is, reference element readings are taken on either side of the optimum time $T_x$ of reading $E_x$, namely at least one before and at least one after (at the same wavelength). These are stored in means 32, regardless of which one is actually closest in time. Computing means 34 then is used to do a regression linear analysis through these reference reflectance points, and the intermediate value that is predicted at the time $T_x$ that element $E_x$ is read, is used for the comparison. In this fashion, the predicted reference reflectance $R_x$, hereinafter the "equivalent reference reflectance", is the closest in time since it is computed as the value that would have been read if the reference reflectance had been read at time $T_x$.

In this alternative procedure, most preferably two reference readings (at the same wavelength) are taken before and three after the optimum test element read time $T_x$, or three before and two after. The highest and lowest of these five are deleted and the linear regression is taken on the remaining three points for the prediction of the intermediate reference at time $T_x$.

The invention has been described in detail with particular reference to preferred embodiments thereof, but it will be understood that variations and modifications can be effected within the spirit and scope of the invention.

What is claimed is:

1. In a method for quantitatively assaying for an analyte in a biological liquid, comprising the steps of
   a) scanning with a light beam a test element bearing a sample of liquid having an analyte of unknown concentration;
   b) scanning a reference element with said light beam;
   c) detecting the amount of light diffusely reflected from said test element and said reference element;
   d) filtering the light beam before or after reflection from said elements and before detection, at a preselected wavelength that is the same for both said test element and said reference element;

e) storing the detected amounts of diffuse reflection for each scanning of the reference element and test element, and f) comparing the detected reflectance of the test element with said stored reference detected reflectance to determine how much analyte is present, said reference element being scanned repeatedly, each time for a predetermined multiple of test elements scanned, a reference reflectance value being stored for each scanning;

the improvement wherein said step e) comprises the steps of always selecting from said stored reference reflectance detections at said wavelength that which is either detected by step c) at a point of time closest to the time at which said test element is scanned at said wavelength in step a), or that which is computed to be the equivalent reference reflectance at the actual time the test element reflectance was read, and comparing said selected reference reflectance detection in said step f) with the detected test element reflectance, whereby the effect of drift in the reading of the reference element is minimized.

2. A method as defined in claim 1, wherein said test elements and said reference element are held on a rotating surface and are moved past said light beam repeatedly by rotating said surface.

3. A method as defined in claim 1, wherein each of said test elements is scanned five times at said selected wavelength.

4. A method as defined in claim 1, wherein said reference element is read at at least two different wavelengths.

5. In an analyzer for quantitatively assaying for an analyte of a biological liquid, the analyzer including a) means for scanning with a light beam a test element bearing a sample of liquid having an analyte of unknown concentration;

b) means for scanning a reference element with said light beam;

c) means for detecting the amount of light diffusely reflected from said test element and said reference element;

d) means for filtering the light beam reflected from the elements at a preselected wavelength that is the same for the test element and the reference element;

e) means for storing the detected amounts of diffuse reflection for each scanning of the reference element and of the test element; and f) means for comparing the detected reflectance of the test element with said stored reference detected reflectance at said selected wavelength to determine how much analyte is present, said reference element being scanned repeatedly, each time for a predetermined multiple of test elements scanned;

the improvement wherein said analyzer further includes means for always selecting from the stored reference reflective detections, either the value detected at the point of time that is closest to the time at which said test element is scanned by said scanning means a), or that which is computed to be the equivalent reference reflectance at the actual time the test element reflectance was read, and for supplying this value to said comparing means f), whereby the effect of drift in the reading of the reference element is minimized.

6. An analyzer as defined in claim 5, and further including a rotating support for said elements and means for rotating said support so that each element is scanned by said light beam repeatedly.

7. An analyzer as defined in claim 5, wherein each of said test elements is scanned five times at said selected wavelength.

8. An analyzer as defined in claim 5, wherein said scanning means scans said reference element at least two different wavelengths.

* * * * *

UNITED STATES PATENT AND TRADEMARK OFFICE
CERTIFICATE OF CORRECTION

PATENT NO. : 5,067,093

DATED : November 19, 1991

INVENTOR(S) : C. Przybylowicz, et al.

It is certified that error appears in the above-identified patent and that said Letters Patent is hereby corrected as shown below:

Column 8, line 39, insert --at-- after "at".

Signed and Sealed this

Twenty-third Day of March, 1993

Attest:

STEPHEN G. KUNIN

*Attesting Officer*   *Acting Commissioner of Patents and Trademarks*